United States Patent [19]
Avignon et al.

[11] Patent Number: 4,971,657
[45] Date of Patent: * Nov. 20, 1990

[54] COMBINED PROCESS FOR THERMALLY AND CHEMICALLY TREATING LIGNOCELLULOSE-CONTAINING BIOMASS AND FOR PRODUCING FURFURAL AND CELLULOSE-CONTAINING FIBER MASSES

[75] Inventors: Gerard Avignon, Agen, France; Wolfgang Jaeggle, Bodnegg, Fed. Rep. of Germany; Horst Steinmüller; Thomas Steiner, both of Leonding, Austria

[73] Assignee: Gesellschaft m.b.H. Voest-Alpine Industrieanlagenbau, Austria

[*] Notice: The portion of the term of this patent subsequent to Apr. 10, 2007 has been disclaimed.

[21] Appl. No.: 194,032

[22] Filed: May 12, 1988

[30] Foreign Application Priority Data

May 12, 1987 [AT] Austria ............................ 1188/87

[51] Int. Cl.$^5$ ...................... D21C 11/00; D21C 11/02
[52] U.S. Cl. ........................................ 162/16; 162/36; 549/490
[58] Field of Search .................. 162/14, 15, 16, 46, 162/84, 83, 36; 549/489, 490

[56] References Cited

U.S. PATENT DOCUMENTS

| | | | |
|---|---|---|---|
| 2,859,108 | 11/1958 | Rosenblad | 162/83 |
| 3,085,038 | 4/1963 | Rovesti | 162/16 |
| 3,532,597 | 10/1970 | Ljunggvist | 162/84 |
| 3,738,908 | 6/1973 | Villavicencio | 162/84 |
| 4,070,232 | 1/1978 | Funk | 162/16 |
| 4,155,804 | 5/1979 | Edge, Jr. | 162/16 |
| 4,366,322 | 12/1982 | Raymond | 549/489 |
| 4,401,514 | 8/1988 | Kenzler et al. | 162/16 |

FOREIGN PATENT DOCUMENTS

3435451 10/1986 Fed. Rep. of Germany.

Primary Examiner—Steve Alvo
Attorney, Agent, or Firm—Ostrolenk, Faber, Gerb & Soffen

[57] ABSTRACT

A process for the thermal and chemical treatment of lignocellulose-containing biomass and for the production of furfural and cellulose-containing fiber masses. In order to ensure a high yield of furfural:

lignocellulose-containing biomass is continuously fed into a cooker containing a cooking liquor and, upon heating of the biomass in a heating zone and guidance of the heated biomass through a consecutive retention zone, cellulose or pretreated biomass is continuously withdrawn from the cooker, cooking liquor is continuously withdrawn from the cooker, the cooking liquor withdrawn is continuously fed to a furfural production plant, and the cooking liquor at least largely freed from pentoses and furfural is continuously returned to the cooker, wherein heating may be effected by direct steam or via the cooking liquor.

16 Claims, 1 Drawing Sheet

COMBINED PROCESS FOR THERMALLY AND CHEMICALLY TREATING LIGNOCELLULOSE-CONTAINING BIOMASS AND FOR PRODUCING FURFURAL AND CELLULOSE-CONTAINING FIBER MASSES

The invention relates to a combined process for the thermal and chemical treatment of lignocellulose-containing biomass and for the production of furfural and cellulose-containing fiber masses, as well as to a plant for carrying out the process.

Such a combined process is known, for instance, from DE-A - 34 35 451 and from EP-B 0 038 317. In DE A 34 35 451, a two-stage process comprising pre-hydrolysis and subsequent chemical hydrolysis is described for the production of celluloses and furfural. According to that process, the material to be hydrolyzed is heated in the presence of a diluted acid at temperatures of below 150° C. until the pentosans obtained have been hydrolyzed to pentoses. Thereafter, a hydrolyzing agent is fed and the temperature is rapidly raised to above 160° C. and maintained there until hydrolysis has been completed. The furfural forming from the pentoses is discharged.

In EP-B - 0 038 317, a process for the production of furfural and other organic compounds from acid hydrolysates of plants, in particular spent sulfite lyes, is described. There, the pentoses contained in the spent lyes are dehydrated to furfural by heating in a reactor to temperatures of up to 300° C.

The reaction course of the formation of furfural from pentosans contained in a lignocellulose-containing biomass comprises two reaction stages, which are favored by the addition of acids. The first stage consists in the absorption of water with the pentosans being converted into pentoses by hydrolysis and the second stage comprises dehydration to transform the pentoses into furfural. With the process according to DE-A - 34 35 451, these two reaction stages take place during the chemical hydrolysis of the biomass. However, due to the drastic reaction conditions prevailing, this partially involves the formation of condensation products from furfural and decomposition reactions of the pentosans. The same disadvantages are found with the process according to EP-B - 0 038 317, in which furfural is formed from the spent lye only upon hydrolysis. Hence follows a strongly reduced furfural yield as compared to the maximum furfural yield theoretically possible, with these two processes on account of the formation of condensation products, which also will have adverse effects if bleached sulfite cellulose is produced.

The invention aims at avoiding these difficulties and disadvantages and has as its object to provide a combined process of the initially defined kind as well as a plant for carrying out this process, by which the formation of secondary products from pentoses in the cooking procedure itself is prevented so as to increase the yield of furfural and with which only a slight amount of bleaching agent is required for the production of bleached sulfite cellulose.

According to the invention, this object is achieved in that lignocellulose-containing biomass is continuously fed into a cooker containing a cooking liquor and, upon heating of the biomass in a heating zone and guidance of the heated biomass through a consecutive retention zone, cellulose or pretreated biomass is continuously withdrawn from the cooker, cooking liquor is continuously withdrawn from the cooker, the cooking liquor withdrawn is continuously fed to a furfural production plant, and the cooking liquor at least largely freed from pentoses and furfural is continuously returned to the cooker, wherein heating may be effected by direct steam or via the cooking liquor.

By the continuous removal of pentoses from the cooker, further reaction to furfural and its condensation products in the cooker itself is prevented. Thereby, the yield of pentoses and, thus, furfural is strongly increased, on the one hand and, at the production of cellulose, the purity of the latter is improved, on the other hand. Hence follows a reduced use of bleaching agent at further processing. Recycling of the cooking liquor enables the continuous separation of pentoses without having to interrupt the thermal treatment of the lignocellulose-containing biomass. Moreover, the depletion of cooking liquor in the cooker is avoided.

According to a preferred embodiment, cooking liquor is withdrawn whose concentration of pentoses is more than 5 g/l and in which the decomposition of the pentoses in the cooking liquor lies below 10%. By choosing the pentose concentration, a defined point of withdrawal results at the cooker, the separation of the pentoses, thus, being adaptable to the reaction conditions prevailing in the cooker, whereby the yield of pentoses and furfural may be optimized.

At the production of cellulose according to the sulfite technique, the cooking liquor advantageously is drawn off the cooker at a temperature ranging between 100 and 150° C., preferably 110° and 130° C. and is supplied to the furfural production plant. On account of the drastic reaction conditions prevailing at the production of cellulose according to the sulfite technique, the removal of cooking liquor from a zone of higher temperature would lead to uncontrolled secondary reactions of the pentoses and, thus, to a reduced yield.

It is likewisely favorable if, at the preparation of biomass pretreated by pre-hydrolysis, the cooking liquor is drawn at a temperature ranging between 120° and 200° C., preferably 130° and 170° C., when applying water pre-hydrolysis, and at a temperature of from 100° to 150° C., preferably 110° to 130° C., when applying acid pre-hydrolysis.

According to a further preferred embodiment, the pentoses contained in the cooking liquor are dehydrated to furfural in the furfural production plant, the substrate obtained is subjected to steam distillation, the remaining cooking liquor is returned into the cooker, and the condensed exhaust vapors are subjected to a single- or multi-stage distillation to separate the furfural.

It is advantageous, if the residual liquid occurring at the single- or multi-stage distillation is returned into the cooker.

Furthermore, it is advantageous, if $SO_2$ incurring in the furfural production plant at the production of cellulose is returned into the cooker. Thereby, the depletion of sulfur dioxide of the cooking liquor present in the cooker is avoided and the constant supplementation of the amount of $SO_2$ that reaches the furfural production plant with the cooking liquor can be omitted.

Preferably, the pentose-containing cooking liquor is guided through the furfural production plant with an overall residence time ranging between 10 and 60 min, preferably between 10 and 25 min, the cooking liquor being heated to a temperature of between 130° and 180° C., preferably between 150° and 180° C., and maintained in this range. Naturally, the content of pentoses of the cooking liquor fluctuates during the heating phase. By determining an overall residence time in the furfural production plant at a predetermined temperature, it has become possible to adapt the dehydration reaction condition to the respective content of pentoses and, thus, to improve the furfural yield.

A plant for carrying out the process according to the invention comprises a cooker, into which a feed duct for lignocellulose-containing biomass and a duct for steam enter and to which there are connected a discharge duct for biomass thermally treated in the cooker as well as a branch duct leading to a heat exchanger, from which a return duct for the cooking liquor departs and runs into the cooker, and a furfural production plant including a pipe reactor, a reaction column and a consecutively arranged distillation means, which pipe reactor is connectable, via an entry duct, and which reaction column is connectable, via a return duct, with the cooker in a conveying manner.

According to a suitable embodiment, the branch duct departs at a site of the cooker at which the concentration of pentoses is larger than 5 g/l and at which the decomposition of the pentoses in the cooking liquor is below 10%.

According to a further suitable embodiment, the distillation means is adapted to be connected with the cooker in a duct-like manner for recycling the liquid separated from furfural. Thus, the distillation residue freed from furfural of the distillation means may be conveyed back into the cooker.

Moreover, it is advantageous if an exhaust vapors duct of the reaction column enters into a collecting basin connected with the distillation means, which collecting basin includes a gas space adapted to be connected with the cooker in a duct-like manner. Thereby, the $SO_2$ incurring at the production of sulfite cellulose may be returned into the cooker.

The process according to the invention and a plant for carrying out the process will be explained in more detail with reference to FIGS. 1 and 2.

BRIEF DESCRIPTION OF THE DRAWINGS

Both Figures represent block diagrams of the plant according to one embodiment each.

According to FIG. 1, a feed duct 2 enters into a cooker 1 to charge the cooker with cooking liquor and biomass. On the upper end of the cooker 1, there enters a steam duct 2' to directly heat the biomass fed. In addition, a discharge duct 3 for removing pre-treated biomass and sulfite cellulose as well as, on a certain level H of the cooker as will be explained later on, a branch duct 5 leading to a heat exchanger 4 provided for heating the cooking liquor are connected to the cooker 1. From the heat exchanger 4, a return duct 6 for cooking liquor departs and runs into the cooker 1, thus closing a heating circuit 7. To the branch duct 5, there are connected in a by-pass like manner a pipe reactor 8 via an entry duct 9 and a reaction column 10 provided in series with the pipe reactor 8 via a return duct 11. From the reaction column, an exhaust vapors discharge duct 12, via a heat exchanger 13, a collecting basin 14 and a further heat exchanger 15, leads to a distillation means 16, which is connected with the cooker 1 via a duct 17 for distillation residues. If the above-described plant is used for the production of sulfite cellulose, the gas space 18 of the collecting basin 14 suitably may be connected to the cooker 1 via a heat exchanger 19 by means of a duct 20 illustrated in the Figures in broken lines.

Figure 1:
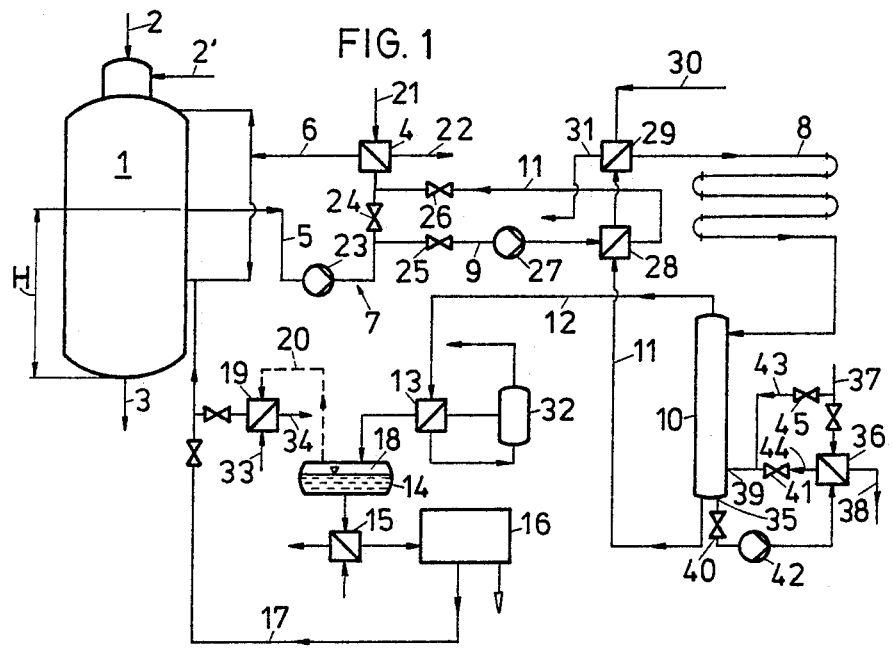

The process according to the invention is performed in the following way:

The cooker 1 is fed with lignocellulose-containing biomass and cooking liquor via feed duct 2, the contents of the cooker being heated by direct steam. Cooking liquor is drawn off the cooker 1 via branch duct 5 for a precise temperature adjustment and is conveyed into the heat exchanger 4, to which high-pressure steam is supplied (represented by arrows 21, 22), is heated there and is conveyed back into the cooker 1 via return duct 6. The circulation of the cooking liquor is effected by means of a pump 23 provided in the branch duct 5. Between the branching of the supply duct 9 and the entry of the return duct 11, a valve 24 is provided in the branch duct, which valve is opened in the starting phase of the cooker 1 at the direct circulation of the cooking liquor over the heat exchanger 4, whereas valves 25, 26, which are provided in the supply duct 9 and in the return duct 11, respectively, are closed.

As soon as pentosans have been hydrolyzed to pentoses at a predetermined concentration and have been dissolved by the cooking liquor, the valve 24 incorporated in the branch duct is closed and the valves 25 and 26 provided in the supply and return ducts are opened such that cooking liquor is continuously pumped into the pipe reactor 8 through supply duct 9 by the aid of a pump 27 arranged in the supply duct 9. During the circulation of the cooking liquor in the furfural production plant 8, 10, 16, lignocellulose-containing biomass is continuously fed to the cooker 1 and the readily treated biomass (or cellulose) is continuously withdrawn.

The height H of the withdrawal site of the branch duct 5 at the cooker 1 is chosen such that the concentration of pentoses in the cooking liquor is larger than 5 g/l and the decomposition of pentoses in the cooking liquor lies below 10%. When processing pretreated biomass, it is taken care at the temperature control within the cooker 1 that the temperature of the cooking liquor withdrawn ranges between 120° and 200° C., preferably between 130° and 170° C., when applying water pre-hydrolysis, and between 100° and 150° C., preferably between 110° and 130° C., when applying acid pre hydrolysis.

The cooking liquor branched off via supply duct 9 is introduced into two heat exchangers 28 and 29 also provided in the supply duct and one (28) of which is supplied with cooking liquor returning via the return duct 11 and the other (29) of which is supplied with high-pressure steam (illustrated by arrows 30 and 31), and thereby is brought to the temperature necessary for the dehydration of pentoses to furfural. This reaction stage primarily takes place in the pipe reactor 8 and partially also in the reaction column 10, into which the cooking liquor is subsequently conducted. In the reaction column 10, the furfural formed is expelled from the cooking liquor by means of steam, i.e., is stripped, then is conducted into the heat exchanger 13 via the exhaust vapors discharge duct 12, is condensed there under the formation of secondary steam, and the aqueous furfural solution forming is collected in the collecting basin 14.

The secondary steam forming in the heat exchanger 13 is condensed in a cooler 32 and is conveyed back to the heat exchanger 13. The cooking liquor freed from furfural and drawn on the lower end of the reaction column 10 is continuously returned into the cooker by means of the return duct 11 via the heat exchangers 28 and 4.

If the plant is operated for the production of sulfite cellulose, it is taken care at the temperature control within the cooker 1 that the temperature of the cooking liquor withdrawn ranges between 100° and 150° C., preferably between 110° and 130° C. Sulfur dioxide incurring in the gas space 18 of the collecting basin 14 is heated in the heat exchanger 19, which is supplied with high-pressure steam as illustrated by arrows 33 and 4, and subsequently is returned into the cooker 1.

The aqueous furfural solution present in the collecting basin 14 is cooled in the heat exchanger 15 under the formation of secondary steam and is fed to the furfural distillation means 16, in which furfural is extracted in one or several stages. The distillation residue incurring is conveyed back into the cooker 1 via duct 17.

The supply of the reaction column 10 with heat suitably may be realized in two ways, both with the production of cellulose and with the preparation of pretreated biomass.

According to FIG. 1, the cooking liquor is withdrawn from the reaction column on the lower end 35 thereof, is heated in the heat exchanger 36 by high-pressure steam (illustrated by arrows 37, 38) and is conveyed back into the reaction column 10 near its lower end 39. Circulation is controlled by means of valves 40 and 41 and a pump 42. From the high-pressure steam supply duct 37, a high-pressure steam branch duct 43 runs into the return duct 44 departing from the heat exchanger 36, a control valve 45 being provided in the high-pressure steam branch duct 43. By the interaction of the valves 40, 41 and 45, hot steam can be used both to supply heat to the heat exchanger 36 and to feed the reaction column 10.

Figure 2:
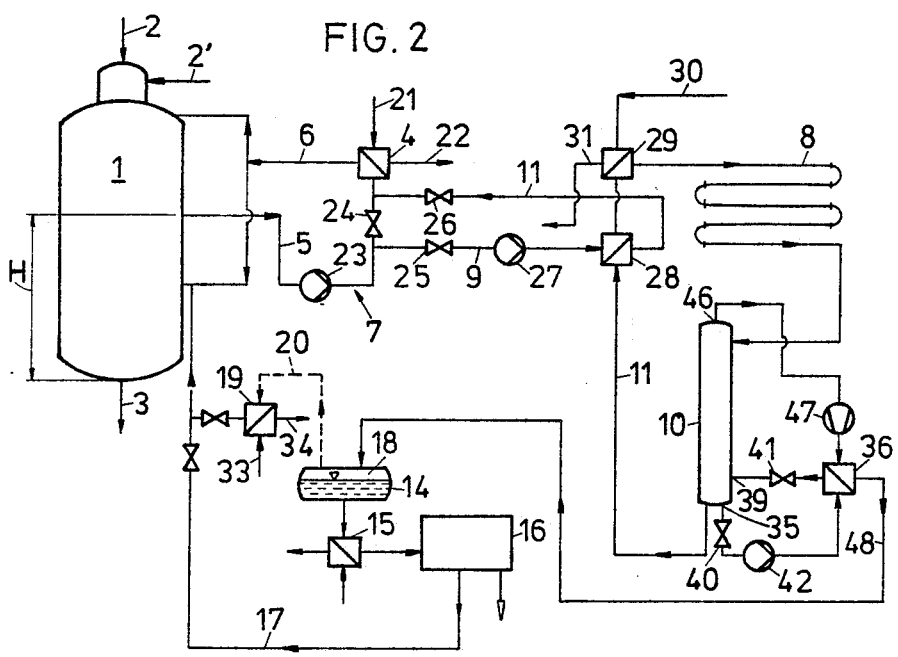

According to FIG. 2, the exhaust vapors leaving the reaction column 10 on its upper end 46 are compressed in a compressor 47 and are used to supply heat to the heat exchanger 36. The exhaust vapors condensed in the heat exchanger 36 subsequently are conducted into the collecting basin 14 via duct 48 and are processed as described above.

What we claim is:

1. A combined process for thermally and chemically treating lignocellulose-containing biomass and for producing furfural and cellulose-containing fiber masses, which process comprises the steps of continuously feeding lignocellulose-containing biomass into a cooker containing cooking liquor and including a heating zone and a consecutive retention zone, heating said biomass in said heating zone, guiding the heated biomass through said retention zone, and continuously withdrawing cellulose or pretreated biomass from said cooker, continuously withdrawing cooking liquor from said cooker, said cooking liquor having a concentration of pentoses of more than 5 g/l and exhibiting a decomposition of pentoses in the cooking liquor of below 10%, to prevent further reaction to furfural in said cooker itself, continuously supplying said cooking liquor to a furfural production plant, dehydrating the pentoses contained in said cooking liquor to furfural in said furfural production plant so as to obtain a liquid substrate, continuously subjecting said liquid substrate to distillation so as to free said cooking liquor from pentoses and furfural at least to a major extent and to obtain remaining cooking liquor and condensed exhaust vapors containing furfural and continuously returning said remaining cooking liquor into said cooker and subjecting said condensed exhaust vapors to an at least single-stage distillation to separate furfural.

2. A process as set forth in claim 1, wherein heating of said biomass is effected by direct steam.

3. A process as set forth in claim 1, wherein heating of said biomass is effected by said cooking liquor.

4. A process as set forth in claim 1 to be applied for the production of cellulose according to the sulfite technique, wherein said cooking liquor is withdrawn from said cooker at a temperature ranging between 100° and 150° C. and is supplied to the furfural production plant.

5. A process as set forth in claim 4, wherein said cooking liquor is withdrawn from said cooker at a temperature ranging between 110° and 130° C.

6. A process as set forth in claim 1 to be applied for the preparation of biomass pretreated by pre-hydrolysis, wherein said biomass is subjected to water pre-hydrolysis and said cooking liquor is withdrawn at a temperature ranging between 120° and 200° C.

7. A process as set forth in claim 6, wherein said cooking liquor is withdrawn at a temperature ranging between 130+ and 170° C.

8. A process as set forth in claim 1, wherein said liqnocellulose-containing biomass is subjected to acid prehydrolysis and said cooking liquor is withdrawn at a temperature ranging between 100° and 150° C.

9. A process as set forth in claim 8, wherein said cooking liquor is withdrawn at a temperature ranging between 100° and 130° C.

10. A process as set forth in claim 1, wherein a residue liquid incurs at said at least single-stage distillation, said residue liquid being returned into said cooker.

11. A process as set forth in claim 4, wherein $SO_2$ incurs at the production of cellulose in said furfural production plant, said $SO_2$ being returned into said cooker.

12. A process as set forth in claim 1, wherein said cooking liquor containing pentoses is guided through said furfural production plant with an overall residence time ranging between 10 and 60 minutes, said cooking liquor being heated to, and maintained at, a temperature of between 130° and 180° C.

13. A process as set forth in claim 12, wherein said residence time ranges between 10 and 25 minutes.

14. A process as set forth in claim 12, wherein said cooking liquor is heated to, and maintained at, a temperature of between 150° and 180° C.

15. A process as set forth in claim 1 wherein said furfural production plant includes a pipe reactor and a reaction column.

16. A process as set forth in claim 1, wherein said substrate is subject to steam distillation.

* * * * *